United States Patent
Blume et al.

[19]

[11] Patent Number: 6,014,580
[45] Date of Patent: Jan. 11, 2000

[54] DEVICE AND METHOD FOR SPECIFYING MAGNETIC FIELD FOR SURGICAL APPLICATIONS

[75] Inventors: Walter M. Blume, Webster Groves; Gerard H. Epplin, St. Louis; Jeffrey M. Garibaldi, Valley Park, all of Mo.

[73] Assignee: Stereotaxis, Inc., St. Louis, Mo.

[21] Appl. No.: 09/020,798

[22] Filed: Feb. 9, 1998

Related U.S. Application Data

[60] Provisional application No. 60/065,102, Nov. 12, 1997.

[51] Int. Cl.$^7$ .................................................... A61B 5/05
[52] U.S. Cl. ......................... 600/424; 600/427; 600/429; 128/899
[58] Field of Search ................................. 600/427, 429, 600/424; 128/899

[56] References Cited

U.S. PATENT DOCUMENTS

| | | | |
|---|---|---|---|
| 3,358,676 | 12/1967 | Frei et al. | 128/1.3 |
| 3,674,014 | 7/1972 | Tillander | 128/2.05 R |
| 4,869,247 | 9/1989 | Howard, III et al. | 128/303.1 |
| 4,923,459 | 5/1990 | Nambu | 606/130 |
| 5,093,754 | 3/1992 | Kawashima | 361/144 |
| 5,125,888 | 6/1992 | Howard et al. | 600/12 |
| 5,334,207 | 8/1994 | Gay, Jr. | 606/7 |
| 5,353,807 | 10/1994 | DeMarco | 128/772 |
| 5,558,091 | 9/1996 | Acker et al. | 128/653.1 |
| 5,654,864 | 8/1997 | Ritter et al. | 361/141 |

FOREIGN PATENT DOCUMENTS

WO 96/03795  2/1996  WIPO.

OTHER PUBLICATIONS

"Characteristics of an Improved Magnetic–Implant Guidance System," Robert G. McNeil et al., IEEE Trans. Biomed. Eng., vol. 42, No. 8, Aug. 1995, pp. 802–808.

"Functional Design Features and Initial Performance Characteristics of a Magnetic–Implant Guidance System for Sterotactic Neurosurgey," Robert G. McNeil et al., IEEE Trans. Biomed. Eng. vol. 42, No. 8, Aug. 1995, pp. 793–801.

"Magnetic Manipulation Instrumentation for Medical Physics Research," G. T. Gillies et al., Rev. Sci. Instrum. 65 (3)Mar. 1994, pp. 533–562.

"Goniometric Motion Controller for the Superconducting Coil in a Magnetic Sterotaxis System," Elizabeth G. Quate et al., IEEE Trans. Biomed. Eng., vol. 38, No. 9, Sep. 1991, pp. 899–905.

"Nonlinear magnetic sterotaxis: Three–dimensional, in vivo remote magnetic manipulation of a small object in canine brain," M. S. Grady et al., Med. Phys. 17 (3) May/Jun. 1990, pp. 405–415.

(List continued on next page.)

*Primary Examiner*—Ruth S. Smith
*Attorney, Agent, or Firm*—Howell & Haferkamp, L.C

[57] ABSTRACT

A device and method for specifying the orientation of a magnetic field produced in a patient to aid surgical procedures involving an implanted magnet. The device includes a processor, a pointing device, a magnet assembly generating a magnetic field, a display, and a medical imaging device that provides three-dimensional imaging of an operating region of a patient during surgery. Fluoroscopic images of an operating region of the patient in which the magnetic delivery vehicle is implanted are shown on a screen, each image representing a projection in space of the operating region. The pointing device is operated to move a cursor from a projection of a present location of the magnetic delivery vehicle to a projection of a desired future location of the magnetic delivery vehicle. When the locations are completely specified, the currents applied to the magnets in the magnet assembly are controlled by the processor to produce a magnetic field to move or orient the magnetic delivery vehicle from the present location towards the desired future location.

13 Claims, 3 Drawing Sheets

OTHER PUBLICATIONS

"External Magnetic Guidance of Endovascular Catheters With a Superconducting Magnet: Preliminary Trials, " A. Gaston et al., J. Neuroradiol, 1988, 15, pp. 137–147.

"A review of medical application of magnet attractions and detection, " Jack Driller et al., Journal of Med. Eng. & Tech., vol. 11, No. 6, Nov/Dec. 1987, pp. 271–277.

"Magnetically Guided Devices for Vascular Exploration and Treatment, " Sadek K. Hilal et al., Radiology 113, Dec. 1974, pp. 529–540.

"Selective Angiography with a Catheter Guided by a Magnet, " H. Tillander, IEEE Trans. On Magnetics, vol. MAG–6, No. 2, Jun. 1970, pp. 355–358.

"Development and Use of the POD Catheter in the Cerebral Vascular System, " J. Driller et al., Medical Research Engineering, Aug–Sep. 1969, pp. 11–16.

"Superconducting Magnet System for Intravascular Navigation, " D.B. Montgomery et al., Journal of Applied Physics, vol. 40, No. 5, Apr. 1969, pp. 2129–2132.

"Symposium on Bioengineering: Magnetic Forces for Medical Applications, " D.B. Montgomery et al., Journal of Applied Physics, vol. 40, No. 3, Mar. 1969, pp. 1039–1041.

"A New Magnet System For 'Intravascular Navigation', " Shyam B. Yodh et al., Med. And Bio. Eng., vol. 6, 1968, pp. 143–147.

DEVICE AND METHOD FOR SPECIFYING MAGNETIC FIELD FOR SURGICAL APPLICATIONS

CROSS-REFERENCE TO RELATED APPLICATION

This application claims the benefit of U.S. Provisional Application No. 60/065,102, filed Nov. 12, 1997, entitled "Device and Method for Specifying Magnetic Field for Surgical Applications," and which is herein incorporated by reference in its entirety.

BACKGROUND OF THE INVENTION

1. Field of the Invention

This invention concerns devices and methods for specifying and applying magnetic fields, and more particularly to such devices and methods useful in the field of stereotactic surgery in which a magnetic delivery vehicle such as a magnetically-tipped catheter or endoscope, or a magnetic seed of another type is used.

2. Description of the Related Art

It is known in the art to provide magnetic manipulation of diagnostic or therapeutic elements (which, for simplicity, we shall herein refer to collectively as "magnetic delivery vehicles") through body tissue or ducts (such as in vascular exploration or treatment). Systems providing for such manipulation are described in a number of previously published articles and patents, such as "Magnetically Guided Devices for Vascular Exploration and Treatment," Sadek K. Hilal et al., Radiology 113, 529–540 (1974); U.S. Pat. No. 3,358,676, entitled "Magnetic Propulsion of Diagnostic or Therapeutic Elements Through the Body Ducts of Animals or Human Patients," issued Dec. 19, 1967 to Ephraim H. Frei et al.; "Magnetic Manipulation Instrumentation for Medical Physics Research," George T. Gillies et al., Review of Scientific Instruments 65, 533–562 (1994); "Characteristics of an Improved Magnetic-Implant Guidance System," Robert G. McNeil et al., IEEE Trans. on Bio. Eng. 42(8) 802–808 (1995); "Functional Design Features and Initial Performance Characteristics of a Magnetic- Implant Guidance System for Stereotactic Neurosurgery," Robert G. McNeil et al., IEEE Trans. on Bio. Eng. 42(8) 793–801 (1995); and U.S. Pat. No. 5,654,864 to Ritter et al., entitled "Control Method for Magnetic Stereotaxis System," issued Aug. 5, 1997. All of these references are hereby incorporated in their entirety by reference.

The cited systems all provide fixed or manually moved or controlled permanent magnets or electromagnets that are capable of applying fields and forces to treatment implants to move or guide the implant through a treatment region. These systems require manual control by a technician in accordance with the instructions of a surgeon during an operating procedure, or by the surgeon himself or herself. It would be desirable to provide a device and a method to simplify the control of the application of magnetic fields to a magnetic delivery vehicle implanted in a patient, so that a surgeon can simply observe a current location of the magnetic delivery vehicle and specify, in an intuitive manner, the next desired location and have magnetic fields applied in a proper orientation to guide, push, or pull (as the case may be) the magnetic delivery vehicle to the next location. It would be particularly useful to provide a surgeon with a device and method for specifying a three-dimensional path for the magnetic delivery vehicle.

SUMMARY OF THE INVENTION

It is therefore an object of the invention to provide a device that provides an intuitive method for specifying an orientation of a magnetic field during a surgical procedure.

It is a further object of the invention to provide a device that allows a surgeon interactive control of magnetic fields applied to a magnetic delivery vehicle while showing representations of the location of the magnetic delivery vehicle and the next intended location on a screen.

It is another object of the invention to provide a device that provides a surgeon with a interactive control of locations of a magnetic delivery vehicle in three dimensions.

It is still another object of the invention to provide methods for displaying a three-dimensional representation of a present location of a magnetic delivery vehicle in a patient and for applying a magnetic field to the magnetic delivery vehicle in response to a three-dimensional representation of next intended location of the magnetic delivery vehicle.

These and other objects are accomplished by the present invention, which, in one embodiment, comprises (a) a processor having an input for at least a first input signal and responsive thereto to generate a current control signal; (b) a pointing device generating at least a pointing device output signal, the pointing device output signal being coupled to the first signal input of the processor; (c) a magnet assembly coupled to the processor and responsive to the current control signal, the magnet assembly generating a magnetic field in an operating region; (d) a medical imaging device coupled to the microprocessor and configured to provide a plurality of images of the operating region during generation of the magnetic field; and (e) a display coupled to the processor and responsive thereto for displaying images from the medical imaging device and a cursor; wherein the processor is responsive to the pointing device output signal for displaying and moving a cursor on the images displayed from the medical imaging device, and for adjusting the current control signal in accordance with vectors defined by selected cursor positions to produce a magnetic field from the magnet assembly in an orientation to guide or move a medical delivery vehicle surgically implanted in a patient and disposed in the operating region.

According to another embodiment of the invention, the invention comprises the steps of (a) displaying a plurality of fluoroscopic images of an operating region of a patient having a magnetic delivery vehicle implanted therein on a screen, each image representing a projection in space of the operating region; (b) for each image, operating a pointing device to move a cursor from a projection of a present location of the magnetic delivery vehicle to a projection of a desired future location of the magnetic delivery vehicle; (c) determining currents in a plurality of magnets arrayed about the operating region to produce a magnetic field to move the magnetic delivery vehicle from the present location to the desired future location; and (d) applying the currents to the plurality of magnets. These steps can be implemented automatically via software control of a computer system.

Further details of the inventive device and method are set forth in the description which follows.

DESCRIPTION OF THE PREFERRED EMBODIMENTS

In this description and in the claims that follow, references to normally conducting coils and to resistive coils are intended to be synonymous, and such coils are intended to be contrasted with superconducting coils.

Figure 1:
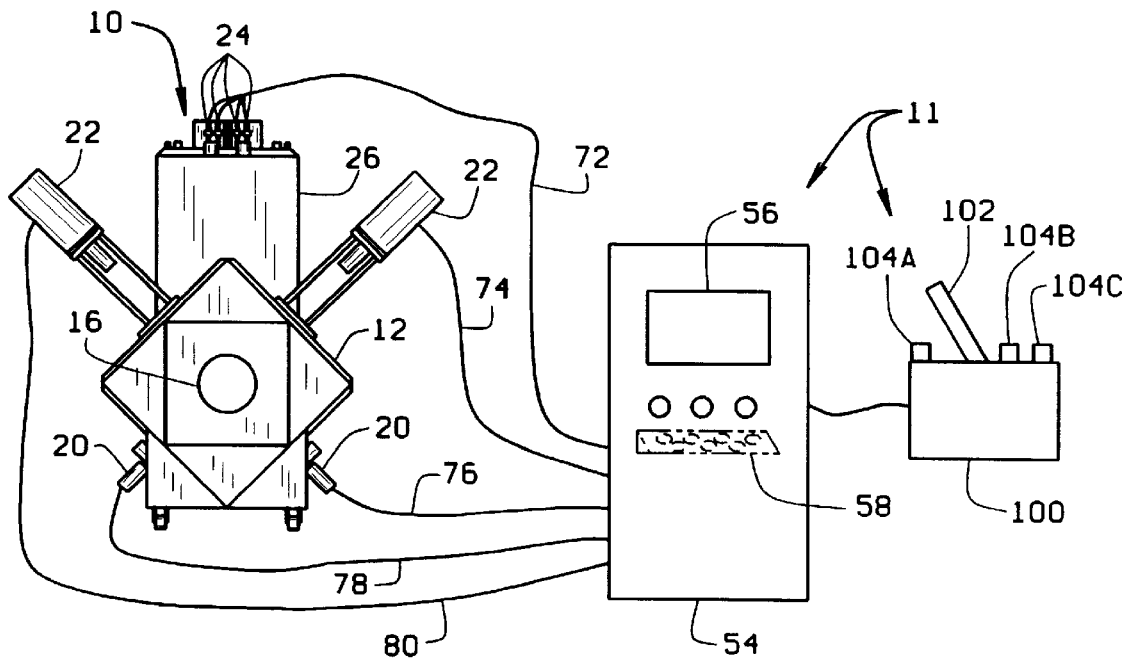
FIG. 1 is a schematic illustration of a magnetic stereotactic surgical (MSS) system incorporating an embodiment of the invention.
Figure 2:
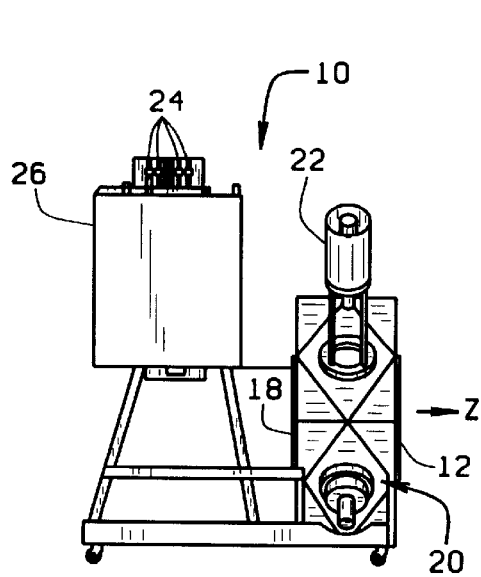
FIG. 2 is a side view of the MSS system of FIG. 1.
Figure 3:
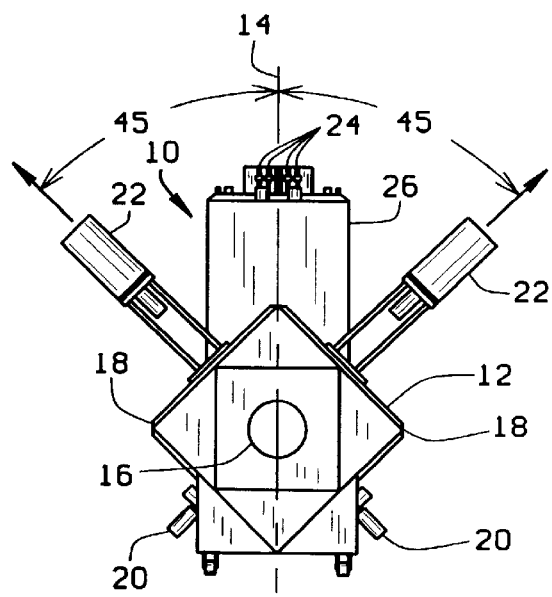
FIG. 3 is a front view of the MSS system of FIG. 1.
Figure 4:
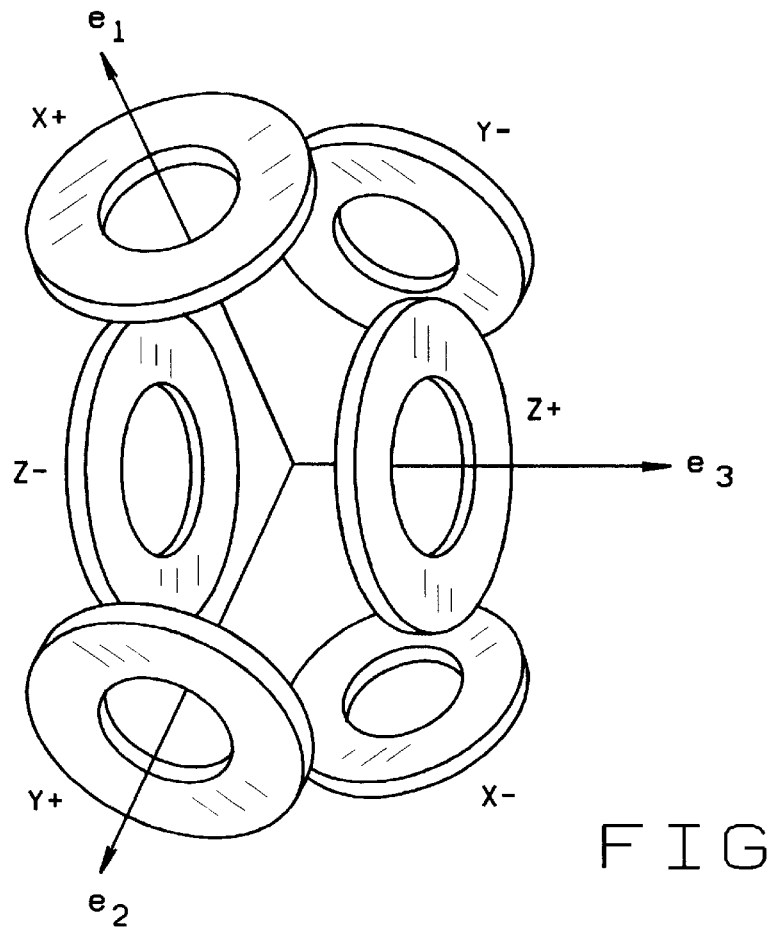
FIG. 4 is a perspective view of the orientation of the electromagnetic coils in the MSS system of FIG. 1.

FIG. 1 shows, in schematic form, a magnetic stereotactic surgical (MSS) system 10 incorporating an embodiment 11 of the present invention. This particular apparatus is designed for brain surgery, but the inventive apparatus could be used for surgery in other parts of the body, as well. The illustrated system 10 includes six resistive or superconducting coils (not shown in FIG. 1) located in a rectangular box or helmet 12. With the Z-axis defined in the direction of the axial component of the head (see FIG. 2), the X- and Y-coil axes are rotated 45° from the sagittal plane 14 of the head, as indicated in FIG. 3. Returning to FIG. 1, the X- and Y-axes are symmetrically located such that the horizontal extensions 22 of the MSS system away from the patient's body are minimized. The vision component of the MSS includes a superposition of pre-operative MRI images referenced by biplanar fluoroscopy cameras 20 linked to a real time host system 54. Both cameras 20 are calibrated to the MSS six-coil helmet design shown schematically in FIG. 4, in which coils X+, X− form one pair of opposing coils; Y+ and Y− form a second pair; and Z+ and Z− form a third, each pair on one of the mutually perpendicular axes $e_1$, $e_2$, and $e_3$, respectively. FIG. 1 also shows that X-ray generators for cameras 20 are located inside magnetic shields 22.

In use, the head of a patient (not shown in FIG. 1) is disposed in opening 16 of apparatus 10. Console 54 contains a processor such as a digital computer responsive to operator commands input by a joystick or other pointing device 100, possibly in conjunction with another input device 58 such as a keyboard. Processor 54 is preferably a standard microcomputer system. Presently available systems such as those based on Intel PENTIUM(R) microprocessors or Sun SPARC(R) workstations are suitable for this purpose. It may be assumed that such microcomputer systems include various input and output devices, as well as memory, disk drives, and other standard computer peripherals, not all of which are shown. However, one skilled in the art would understand that many other types of processors can be substituted for those specified herein, including, but not limited to, special purpose processors, and that certain peripheral devices commonly used with microcomputer systems, other than those explicitly shown in FIG. 1, may be omitted to reduce costs. Instructions necessary for the operation of processor 54 may be stored in any suitable form for use by processor 54, such as on a disk or diskette, or in ROM or CDROM, depending upon the type of processor 54 that is used and the type of accompanying peripheral devices and internal memory that is provided.

Processor 54 is configured to be responsive to operator commands from pointing device 100 (and possibly other input devices such as keyboard 58) as well as to cameras 20 for controlling display 56 and for controlling power supplies that provide currents to coil terminals 24 to generate the required magnetic fields in the electromagnetic coils to control movement of a magnetic delivery vehicle (MDV, not shown) in the portion of the body undergoing surgery. Connections 72, 74, 76, 78, and 80 represent connections between processor 54 and various devices within MSS apparatus 10, including connections to control the fluoroscope generator tubes and to receive real-time images from imaging plates, connections to control coil currents, and various other connections, not all of which are germane to this invention.

Figure 5:
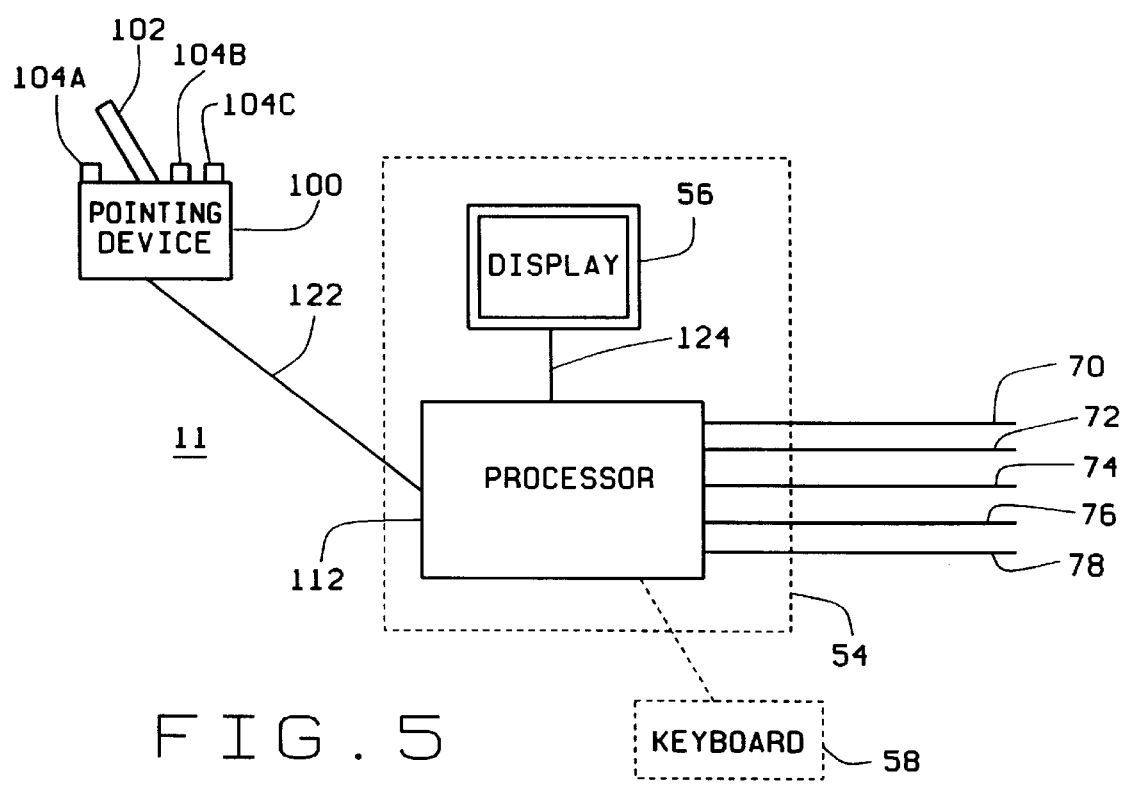
FIG. 5 is a more detailed block diagram of a portion of the embodiment of the inventive magnetic field specification system included in the system of FIG. 1.

The pertinent portion 11 of the apparatus shown in FIG. 1 is shown in greater detail in FIG. 5. The inventive apparatus comprises, in one form, a microcomputer or other suitable processor 112, an optional keyboard 58 (which may be necessary for other functions of processor 112, but is optional for purposes of the present invention), a pointing device 100, and a display 56.

Processor 112 is provided with at least one input which is fed through signal link 122 by pointing device 100. Pointing device 100 may be a standard joystick with a moveable arm 102 and preferably also three pushbuttons 104A, 104B, and 104C. A computer mouse is another example of a pointing device, and still others suitable for use will be known to those skilled in the art. Some that provide particular advantages are described in greater detail below, but the present description will assume that pointing device has a moveable arm 102 and buttons 104A, 104B, and 104C that work independently.

It should be understood that signal link 122 carries "a signal" from the pointing device 100 to the processor 112. Pointing device 100 may typically provide an analog voltage or resistance that can be measured using an analog-to-digital (D/A) converter in processor 112, or it may provide a serial or parallel digital output signal. The state of pushbuttons 104A, 104B, and 104C may appear on a separate line, or it may be represented as part of a bit stream in which the orientation of moveable arm 102 is represented, for example. Because of the wide variety of implementations possible, and because the nature of the signal does not form a part of the invention, we shall simply assert for the purpose of this discussion that the pointing device 100 encodes orientation information (which we shall define as including information about the state of the pushbuttons) as a "pointing device output signal" and conveys this signal to "an input" of processor 112.

Processor 112 is also provided with a display device 56, which may be a standard computer CRT or LCD display screen, or a suitable substitute. The display screen displays, among other things, fluoroscopic information from fluoroscopic imaging devices in MSS apparatus 10 received by processor 112.

Figure 6:
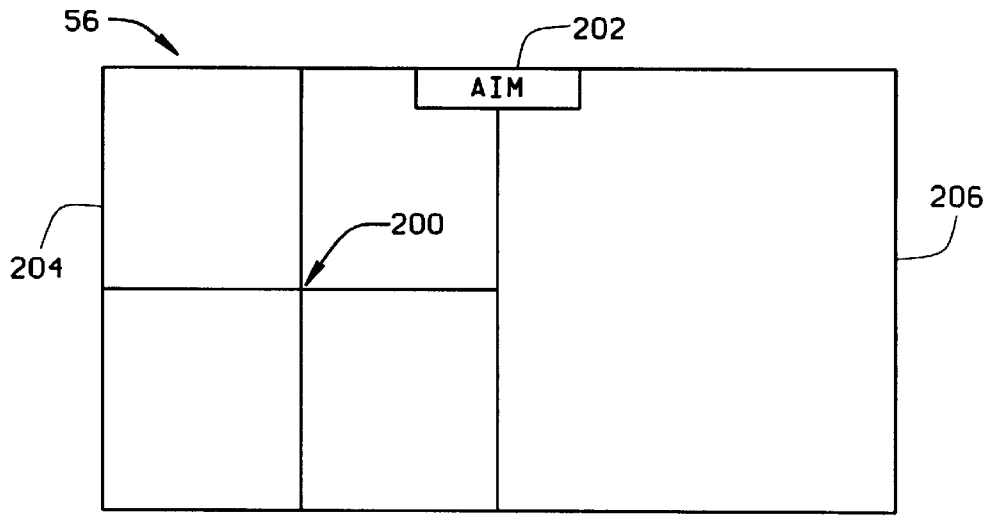
FIG. 6 is a drawing of the display included with the system of FIG. 5 showing a crosshair cursor and the division of the display into X- and Y-planes.

As shown in FIG. 6, display 56 is set up to display X and Y views (204 and 206, respectively) of the operating region side-by-side on a divided screen. A cursor 200 is displayed, which may preferably be a crosshair-type cursor. Cursor 200 is controlled by processor 112 in response to movement of the joystick handle 102 or other pointing device motion. (For simplicity, it shall be assumed for the present discussion that a joystick 100 is the pointing device. However, those skilled in the art will recognize generalizations that may be made for other pointing devices.) The joystick handle 102 ranges the cursor over the full range of the selected image at a given time, with a means of switching the axis provided. An indication 202 of the system state is preferably displayed across the middle of the top of display 56. Buttons 104A, 104B and 104C are, for convenience, assigned various functions. For example, button 104A may be assigned to a shut-down function, so that processor 112, in response to a push of button 104A, ramps the coils down to zero current.

The system itself can be three major states defined by software control of processor 112, although it is not intended that the system be limited to only three major states, as future improvements may warrant the inclusion of additional major states. The three major states presently contemplated are: "AIM," "RAMP," and "MOVE." It will be understood by those skilled in the art that the steps described below are carried out with the aid of software control, the software being a stored program that is executed by processor 112.

Figure 7:
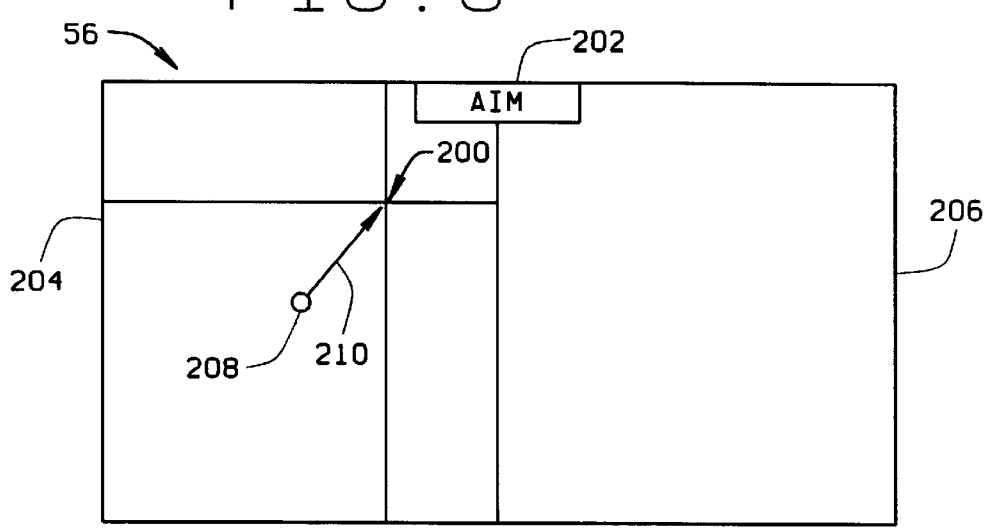
FIG. 7 is a drawing of the display of FIG. 6 showing how a seed is located and how an intended next position for the seed is specified in the X-plane.
Figure 8:
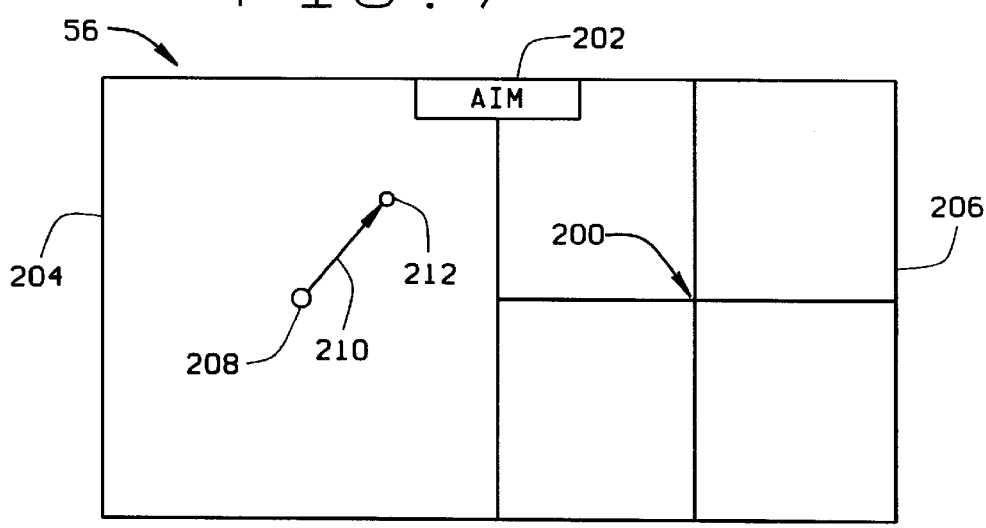
FIG. 8 is a drawing of the same display as shown in FIG. 7, showing the system ready to accept a similar specification of location and intended location in the Y-plane.

The "AIM" state is the initial state. In operating the system, a surgeon selects a position of an MDV (magnetic delivery vehicle, such as a magnetic tip of a catheter) and a desired direction of movement in this state. Using joystick handle 102, the surgeon moves the cursor over the current location of the MDV on either the X- or the Y-axis on display 56. The surgeon then presses and holds a button DRAG__BTN, which may, for example, be button 104B on joystick 100. As represented in FIG. 7, software running in processor 112 responds by causing a small green circle 200 to appear on display 56 marking the position of the MDV. (The colors selected for this description are not the only possible colors, but have been selected for clarity and the convenience of a surgeon operating the system, assuming that a color display 56 is provided. Any other color indication scheme may be used, but colors that might cause confusion during a surgical procedure should, of course, be avoided.) A green line 210 is then formed between the MDV position and the current position of the cursor, moving as the cursor is moved in response to joystick handle 102. When the surgeon has moved the cursor to the target position, he releases DRAG__BTN (i.e., button 104B). The green circle marking the MDV location and the green line indicating the intended movement remain at the position they were at the time DRAG__BTN (button 104B) was released. Also, as shown in FIG. 8, a small green dot 212 marks the target location. The line dragging operation can be repeated as many times as necessary. If the surgeon wishes to change the selected MDV position or target position, he simply repeats the line dragging operation. Pressing DRAG__BTN again erases the previous markings and redraws the MDV at the current cursor position.

Once the intended movement has been defined on one axis, the surgeon performs an almost identical operation on the other axis. Before the surgeon presses DRAG__BTN (button 104B), the surgeon drags a line from the MDV location on display 56 to the target position. Both the MDV position and the target position must correctly reconstruct to points in 3-dimensional space. (To correctly reconstruct, the arrows in the X- and the Y-portions of the display must be able to project, within a preselected error tolerance, onto a single arrow in three-dimensional space. If they can be projected in this fashion, then the two arrows represent the three-dimensional arrow pointing in the direction of desired MDV movement. Otherwise, at least one of the arrows in the one of the two portions of the display is in error.) If the MDV position does not reconstruct properly, an indication will be provided on screen 56, such as by a color change of the MDV circle from green to red. The surgeon then releases DRAG__BTN (button 104B) and restarts the process, repositioning the cursor over the correct location of the MDV. If an incorrect target position is selected, the line and the target dot will be indicated as incorrect, such as by drawing it in red on display 56. The surgeon may have to repeat the line dragging operation until the MDV position, the line, and the target dot are all indicated as being correct (e.g., drawn in green).

Properties of the crosshair cursor may also be used as a condition indicator. For example, a green crosshair cursor may be used to indicate that movement is not yet defined on the opposite axis (e.g., if movement is defined on the X-axis but not the Y-axis). If the movement on the opposite axis is defined, and the DRAG__BTN (button 104B) is not pressed, the cursor is green if the cursor position correctly reconstructs with the MDV position defined on the other axis; otherwise the cursor is shown in red. If the DRAG__BTN (button 104B) is pressed, the crosshair cursor is green if its location matches the target position on the opposite axis; otherwise it is red.

To assist the surgeon in selecting MDV and target locations, tick marks may be placed at the top and bottom of display 56, defining imaginary lines between them. When the surgeon is selecting the MDV position (i.e., when DRAG__BTN is not pressed), the tick marks identify the line on which the MDV must lie to match with the MDV on the other axis. When the surgeon is dragging a line to the target position, the tick marks identify the line on which the target position must lie to match the target position on the other axis. Given a selected MDV or end position on the opposite axis, the MDV or end position on the axis being defined must be somewhere along the line defined by the tick marks. These tick marks are determined in accordance with the three-dimensional projection requirements discussed above.

The surgeon can go back and redo the drag operation on either axis simply by moving the cursor over the image to be redefined. The MDV and target positions on the non-selected axis are always assumed to be correct; e.g., if the surgeon defines the positions on the Y-axis, then moves the cursor to the X-axis image, the Y-axis markings become green regardless of their previous states, and the X-axis markings become green or red depending upon whether they match those on the Y-axis. Thus, the markings on the opposite axis are always assumed to be correct.

When the surgeon is satisfied with the desired movement indicated on both axes, he presses the RAMP__BTN (button 104C). This transitions the system to the "RAMP" state. During the RAMP state, current in the coils ramp to the necessary currents, such as in accordance with methods described in co-pending App. Ser. No. 08/921,298 to Ritter et al., filed Aug. 29, 1997 and entitled "Method and Apparatus for Rapidly Changing a Magnetic Field Produced by Electromagnets," which is hereby incorporated by reference in its entirety. The word "RAMP" or some other indication preferably appears on display 56 to indicate that current ramping is occurring. The calculations needed to determine the current values to which the coils are to be ramped may be similar to those described in co-pending App. Ser. No. 08/920,446 to Werp et al., filed Aug. 29, 1997 and entitled "Method and Apparatus for Magnetically Controlling Motion Direction of a Mechanically Pushed Catheter," and which is also incorporated herein by reference in its entirety. It should be noted that the latter-named application describes a system in which a planned path is selected in advance and position feedback is used to guide a seed or catheter tip along the planned path. The present system differs from that of the latter-named application in that no path is selected in advance, but rather a surgeon guides an MDV in step-bystep increments along a path selected in an ad hoc fashion. However, the calculations needed to determine coil currents in the 08/920,446 application can be employed in a step-by-step fashion without employing the feedback technique described therein.

When ramping is complete, the system transitions to the "MOVE" state.

During the MOVE state, the surgeon moves the guidewire of the MDV to the desired position. Currents in the magnet coils remain on in this state. The system transitions to AIM state when the surgeon again presses DRAG_BTN (button 104B), thereby defining the next move of the MDV. Of course, the system can be shut down when it is no longer needed if the surgeon presses the SHUTDOWN_BTN (button 104A).

In another embodiment of the invention, a three-dimensional input device is substituted for the joystick 100 described above. A suitable three-dimensional input device is the SPACEBALL 3003(TM) 3-D input device manufactured by Spacetec IMC Corporation, Lowell, Mass. This device is a compact desktop input device that can be used to control three-dimensional graphic images, eyepoints, or viewpoints. The device comprises a ball mounted on a base. Force sensors in the ball compute the direction of rotation, allowing a simple conversion to rotation in three dimensions. The spaceball can be used to interactively adjust a representation of a path in three dimensions on a multiplicity of displays, including three-dimensional models of objects, two-dimensional X-rays of objects (such as those described in conjunction with the joystick implementation above), and two-dimensional planar MRI (magnetic resonance imaging) sections of an object. The three-dimensional arrow indicating a desired path may appear as a projection on two-dimensional views, or it may appear to float in front of the views as an aid to orientation). The arrow appears at the point of interaction with the tip of a magnetically tipped implant.

In yet another embodiment of the invention, a surgeon may be provided with a wand and a button on a wand (or a foot pedal) which can be pointed at an object. The orientation of the wand can then be changed to apply a corresponding direction for a path of a magnetic implant. Such wands are presently available with an array of LEDs that emit signals that are sensed by a localizer that comprises an array of cameras. (A three-dimensional localizer apparatus suitable for this purpose is the PIXSYS(TM) 5000 available from Image Guided Technologies of Boulder, Colo.) The position and orientation of the wand in space can be computed using triangulation from the image sensed by the cameras. Preferably, changes in orientation of a magnet field are actually applied only when a switch is depressed, such as a foot switch or a button on the wand or elsewhere. Any object can be "registered" with the wand by pointing to calibration points on the object. Different objects would have differing dimensions of the calibration points, allowing them to be automatically registered. The function of the wand could be made object-specific. To activate the wand, the surgeon would place the wand within some proximity of an object such as a patient's head. Alternately, the wand could be activated merely by pointing at the object. For example, pointing at a patient's head and clicking a button would activate orientation computations relative to the position of the patient's head in space, pointing then to an MRI of the patient would activate orientation relative to the flat plane of the MRI.

There also exist wands that sense location and orientation by sensing an applied magnetic field. Such wands may be used, in conjunction with an applied magnetic field, in this invention, as well.

Instead of a wand, the same sort of activation could be applied by means of a position-sensing glove that can be worn by the surgeon, so that he or she never has to pick up any other object like a wand.

In another variation of the invention, a "virtual catheter" used in place of the joystick could be supplied with a shape similar to an actual magnetic tipped catheter being used for a surgical procedure. For the convenience of the surgeon, the virtual catheter could be made larger than the actual catheter. The virtual catheter could be provided with sensing elements (e.g., a piezoelectric sensor, such as polyvinyldiflouride) that sense bending of the virtual catheter. Electrical signals resulting from this bending could be sent to the processor, which would then convert the bending to corresponding magnetic fields to be applied to the actual tip that would result in the actual catheter being directed in the surgical procedure in a direction corresponding to the bending of the virtual catheter.

In yet another variation of the invention, an articulated magnet could be controlled to generate a magnetic field rather than a set of fixed electromagnets. The magnetic field could be controlled by robotic movement of the articulated magnet.

Other variations and modifications within the spirit of the invention will be apparent to those skilled in the art. Therefore, the examples provided in the specification should be considered as exemplary embodiments. The scope of the invention should be determined by reference to the claims below, and the full scope of equivalents permitted under applicable law.

What is claimed is:

1. A method of specifying a magnetic field to move or guide a magnetic delivery vehicle surgically implanted in a patient comprising the steps of:
   (a) displaying first and second fluoroscopic images of an operating region of a patient having a magnetic delivery vehicle implanted therein, the first and second fluorscopic images each representing a projection in space of the operating region;
   (b) for each of the first and second fluoroscopic images, moving a cursor from a projection of a present location of the magnetic delivery vehicle to a projection of a desired future location of the magnetic delivery vehicle, thereby indicating a target path associated with each of the first and second fluoroscopic images;
   (c) determining whether the target path associated with the first fluoroscopic image and the target path associated with the second fluoroscopic image project within a preselected error tolerance onto a single arrow in three dimensional space, and displaying a result of the determination;
   (d) calculating the currents in a plurality of magnets arrayed about the operating region needed to produce a magnetic field to move or guide movement of the magnetic delivery vehicle from the present location to the desired future location; and
   (e) applying the currents to the plurality of magnets.

2. The method of claim 1, and further comprising displaying tick marks identifying a line on which a target position must lie on the second fluroscopic image to reconstruct, in conjunction with a selected target position on the first fluoroscopic image, a single arrow in three dimensional space.

3. The method of claim 1, further comprising moving a guidewire of the magnetic delivery vehicle to the desired future location.

4. A device for specifying the orientation of a magnetic field in a patient to aid surgical procedures involving an implanted magnetic delivery vehicle, the device comprising:

(a) a processor;

(b) a pointing device coupled to the processor;

(c) a magnet assembly coupled to the processor to produce a magnetic field in an operating region of a patient;

(d) a medical imaging system coupled to the processor and configured to produce an image of the operating region of the patient; and (e) a display device coupled to the processor;

wherein the processor is configured to be responsive to the pointing device to display a movable cursor on the display device, to be responsive to the medical imaging system to display a medical image on the display device, and to be responsive to vectors defined by cursor positions selected with the pointing device to control the magnet assembly to produce a magnetic field in an orientation to guide or move a magnetic delivery vehicle surgically implanted in a patient and disposed in the operating region, and further wherein the medical imaging system produces at least two planar projections of a region of interest for display on the display device, and wherein the cursor is positionable on each of said proiections to thereby allow operator definition of a desired movement in each of said planar projections, and the processor is configured to compare cursor positions indicating a desired movement on each of the projections to determine the feasibility of the desired movement in physical space, the processor further being configured to indicate the feasibility of the desired movement on the display device.

5. The device of claim 4 further comprising an input device for an operator to initiate generation of the magnetic field to thereby achieve the desired movement or guidance of the magnetic delivery vehicle.

6. The device of claim 5 wherein the input device further comprises an input for an operator to interrupt generation of the magnetic fields.

7. The device of claim 6 wherein the input device further comprises an input for an operator to indicate the start of another selection of a desired movement.

8. The device of claim 7, wherein the input device comprises a plurality of pushbuttons.

9. The device of claim 4 further comprising an operator input device configured for an operator to control generation of the magnetic fields.

10. A method for specifying the orientation of a magnetic field to be produced by a magnet system within an operating region in a patient to aid a desired movement of a magnetic medical device therein, the method comprising:

identifying the desired direction of movement by identifying a desired new position for the magnetic medical device on at least two different planar images of the operating region from different points;

determining a direction vector between a current position of the magnetic medical device and the identified desired new position.

11. The method according to claim 10 wherein the step of identifying the desired new position for the magnetic medical device comprises moving a pointer on each planar image to the desired new position.

12. The method according to claim 10 wherein the step of identifying the desired direction of movement includes identifying the current position of the magnetic medical device on at least two different planar images of the operating region.

13. The method according to claim 10 wherein when the desired new position of the magnetic medical device is identified on one planar image, a line on which the desired new position planar must lie in the second planar image is displayed to facilitate identification of the desired new position on the second planar image.

* * * * *